United States Patent [19]
Altchek et al.

[11] Patent Number: 5,583,110
[45] Date of Patent: Dec. 10, 1996

[54] DETECTION OF NEOPLASMS BY HORMONAL TUMOR STIMULATION TEST

[76] Inventors: Albert Altchek, 1050 Fifth Ave., New York, N.Y. 10028; Michael Balkin, 25 Neptune Blvd., Long Beach, N.Y. 11561

[21] Appl. No.: 201,270

[22] Filed: Feb. 24, 1994

Related U.S. Application Data

[63] Continuation-in-part of Ser. No. 193,231, Feb. 8, 1994, abandoned.

[51] Int. Cl.$^6$ .......................... A61K 38/08; G01N 33/68; G01N 33/74
[52] U.S. Cl. ................................ 514/15; 436/64; 436/86
[58] Field of Search ....................... 514/310, 15; 436/64, 436/86

[56] References Cited

PUBLICATIONS

Waxman et al. *British Med. J.* 291:1387–1388. Nov. 1985.
Conn et al. *New England J. Med.* 324(2):93–103. Jan. 1991.
Mayer et al. *Obstetrics and Gynecology* 75(3);529–531. Mar. 1990.
Barbot et al. "Pentagastrin Stimulation Test and Early Diagnosis of Medullary Thyroid Carcinoma . . ."*J. Clin. Endocrinology and Metabolism.* 78(1):114–120. 1994.
Leung et al. "Intercellular Signaling in thte Gonads", *Endocrine Reviews.* 13(3):476–498. Aug. 1992.
Ohno et al. "Presence of gonadotropin–releasing hormone and its messenger ribonucleic acid in human ovarian epithelial carcinoma", *Am J Obstet Gynecol.* 169(3): 605–611. 1993.
Adelson et al. "Effects of Gonadotropin–Releasing Hormone Analogues on Ovarian Epithelial Tumors", *Clin. Obstetrics and Gynecology.* 36(3):690–700. Sep. 1993.
Emons et al. "Gonadotropin Releasing Hormone Binding Sites in Human Epithelial Ovarian Carcinomata", *Eur J Cancer Clin Oncol.* 25:215–221. 1989.

*Primary Examiner*—S. Mark Clardy
*Attorney, Agent, or Firm*—Mitchell A. Stein

[57] ABSTRACT

A method for screening for cancer, a cancer test, a screening system a patient monitoring system and medicinal dosage form for measuring stimulating a specific, detectable response from a stimulus-responsive neoplasm, comprising administering a neoplasm-affecting treatment, in sufficient quantity to stimulate the response; and drawing a blood sample at a time after administration sufficient to distinguish the response. Administering a GnRH analog to a woman prior to measuring circulating serum tumor markers for ovarian epithelial carcinoma provides an improved screening result.

16 Claims, No Drawings

DETECTION OF NEOPLASMS BY HORMONAL TUMOR STIMULATION TEST

CONTINUING DATA

The present application is a continuation-in-part of U.S. patent application Ser. No. 08/193,231 filed Feb. 8, 1994, abandoned, and expressly incorporated herein by reference.

FIELD OF THE INVENTION

The present invention relates to the field of early detection of cancer in humans prior to full presentment of the disease, for continued monitoring after presentment, and as a preoperative confirmation of the disease. More specifically, this invention relates to dosage forms, methods of administration, assays, screens and kits for the detection of certain neoplasms. Even more specifically, this invention relates to the detection of ovarian carcinomata through the acute stimulation of production of specific cancer markers (e.g., CA 125) or distinguishing tumor products (e.g., inhibin) via administration of tumor stimulating agents (e.g., the GnRH analogs leuprolide and nafarelin).

BACKGROUND OF THE INVENTION

Cancer is a disease of monumental proportion and a leading cause of death in the world population. Of the estimated 1,130,000 people in the United States diagnosed in 1992 as having cancer (excluding skin cancer), about half of them will die from these diseases. Smart, et al., "Cancer Screening and Early Detection," *Cancer Medicine*, (Chapter VII, p. 408, Holland, et al. editors, 1993).

In response to this cancer threat, the medical community has sought the development and employment of a number of tools for screening and early detection of neoplasms (i.e., benign or malignant tumors) to facilitate early treatment, especially when there is a high cure rate. In other words, it has long been a goal to determine whether a person has a cancer before the person becomes symptomatic (and is thus asymptomatic) or the cancer has grown to the point of becoming advanced, difficult to treat and with a poor prognosis.

Likewise, after a patient has become symptomatic of cancer, screening follows. However, screening tests are not always conclusive of the existence and type of cancer besetting the patient. Thus, typically a diagnosis is preceded by a regime of various screening and diagnostic tools (including, e.g., physical examinations, exploratory surgery, medical imaging, assays, and the like). The results of the regime are evaluated by the physician or team, and a diagnosis is formulated. There is, quite unexpectedly, no limit to diagnostic tools providing overlapping information, since confirmation of a condition, prognosis and treatment are all critical. Certain of these tools are less intrusive than others. Thus, serum assays (and assays of other biological samples) play an important role in the diagnostic process of a patient that has become symptomatic in better determining the type, nature and progress of the disease.

Lastly, where a patient with a carcinoma has received therapy (e.g., surgery, chemotherapy, radiation therapy, hyperthermia, and the like), in certain instances it is important to monitor the progress of the post-therapeutic patient to determine the status or recurrence of the cancer. Accordingly, screening methods are employed to, among other things, assay (i.e., qualitatively and/or quantitatively test for cancer indicators) serum of such patients to detect, as early as possible, indicators of exacerbated or relapsing disease after primary treatment is given, or even proper response to such treatment (e.g., chemotherapies).

The carcinomas for which early detection would potentially improve diagnosis include ovarian cancer, breast cancer, prostatic cancer, and pancreatic cancer. Ovarian carcinoma, common in Western countries, has a high mortality rate and thus is of great interest and concern to medical science and particularly to gynecology and medical endocrinology. Ovarian cancer is usually diagnosed at a late stage when it is widespread and after the disease has presented itself clinically. This situation is due primarily to the inaccessibility of the ovaries to physical examination and because early localized cancer has no symptoms. Thus, as a tumor mass starts to grow it is virtually transparent to the patient and does not cause pain or symptomatically interfere with other organs. Screens for ovarian cancer include transvaginal ultrasound for high risk cases, serum markers, transpelvic ultrasound and physical examination. Certain of these examinations are generally too expensive for screening of random populations (specifically ultrasound), others are generally unreliable as a screen (physical examination), and still others offer false positives for ovarian cancer (like most ultrasonic methods).

Prediagnostic tests include imaging (X-ray, ultrasound, MRI), and exploratory surgery (laparoscopy and laparotomy). When the results are assembled, a tentative diagnosis ensues, which must be confirmed by histological analysis. Any screening test that allows improved sensitivity and selectivity renders the test reliable for large populations and possesses obvious utility for cancers in general, and ovarian cancer in particular. Since cancer is typically clinically diagnosed after it is apparent, a screening test that allows an earlier diagnosis and a proper therapeutic regime to prevent exacerbation of the condition and an early remission are very desirable goals for this disease.

Similarly, breast cancer is often not detected until a palpable mass is discovered either by a patient's own physical examination or during a physician's physical examination. Further, while mammography is presently employed in screening for breast cancer, it is not without risk, e.g., radiation-induced malignancies, has a relatively high cost especially since a trained radiologist or team must evaluate each film, and is of limited value in pre-menopausal women. Therefore, a screening test for determining the existence of breast cancer indicators prior to the presentation of a lump has obvious utility, and can provide a basis for early diagnosis and non-surgical treatment regimes.

Also, prostatic cancer is the most frequently diagnosed cancer in men in the United States (after skin cancers), second only to lung cancer in Canada, and thus is of great concern. A difficulty encountered in screening for prostatic cancer involves benign prostatic hypertrophy, a condition which causes enlargement of the prostate gland and often is accompanied by urethral constriction. Therefore, physical examination by a doctor and/or diagnosis based on symptomatology is inadequate due to the low selectivity of the physical examination and the presentment of symptoms as an indicator of malignancy. There is at least one known blood test for prostate-specific antigen ("PSA") which is presently employed for screening. However, PSA has equivalent sensitivity as digital rectal examinations ("DRE"), and thus sensitivity for early diagnosis of prostate cancer is low. Accordingly, any screening test to increase sensitivity and early diagnosis of prostate cancer has obvious utility and is a sought after goal of the medical community.

Pancreatic cancer is amongst the worst known cancers in man, since presentation is usually followed by an uncomfortable and rapid death. There is no medically recognized screen for pancreatic cancer, nor any treatment other than palliative measures and pain relief. Accordingly, without doubt, an effective screen that in any sense improves the ability of a physician to detect pancreatic cancer at an early stage, may allow for effective treatment in a situation presently lacking any hope for cure by identifying the disease at an early stage.

As a consequence of the metabolic derangement associated with malignancy, malignant cells often inappropriately produce proteins and other substances that, while having no recognized biological value under the circumstances, nonetheless are associated with the particular malignancy (called "tumor-specific markers"). Thus, it is extremely helpful to have a test that searches for the presence of such tumor specific markers, then compares the quantities found against a base line from the patient and/or from a statistical data base, and thereby allows a determination of the probability of the existence of the tumor. The goal of such a screening test is high sensitivity such that no diseased patient remains undiagnosed. However, if the selectivity is insufficient, the screen becomes inappropriate for general patient population use, since the number of false positives is unacceptably high. By definition, a false positive is only detected after further diagnostic follow-up, which may be both costly and inconvenient as well as emotionally traumatic to the patient. It remains a well recognized goal of any medical screening program to reliably diagnose a condition or disease, while minimizing the cost to society and burden to the patient, through techniques that are both sensitive and selective.

Existing serum screens for cancers normally seek to detect the presence of a tumor-specific antigen by the use of an antibody-based assay. Thus, the antibody seeks to bind with an antigenic determinant (usually a portion of the tumor specific marker) which is instrumental in the detection procedure. "Assays" are processes for measuring the serum level of antigenic determinant, which, when outside the defined normal boundaries, are suggestive of disease. Assays and screens are by definition well-known to the art. However, there is always a need to create new or improved specific chemical, biochemical, or immunochemical compositions, procedures, kits and the like, or combinations thereof, which assist in determining serum levels of specific tumor markers. Since it is believed possible to produce and/or provide antibodies that are each specific for different antigenic determinants, and since a number of different antigens may be present in the biological sample, there is also room to test a single sample for the presence of a plurality of antigens. Accordingly, it is known in the art to create a kit that allows for testing a single serum sample for the presence of a plurality of serum antigens. This kit can be used for determining the presence of a number of different diseases, or for simultaneous detection of a number of markers indicative of the same or other diseases in order to improve the sensitivity and selectivity of the procedure.

It is known that hormonally responsive cells can be stimulated using hormone receptor agonists. It is also known that certain tumors are hormonally responsive, because such tumors possess receptors and the mechanisms for responding to such receptor stimulation. As a consequence of the abnormality of tumor cells, response by such cells to hormone stimulation may be aberrant. Therefore, the art has suggested specific examples, in which a response to a hormone stimulation test through the release of a significantly increased amount of a predetermined substance may be diagnostic for the condition. In other words, in a positive result for a stimulation test, an agonist is administered and the agonist causes the tumor cell to release a significantly increased amount of the predetermined substance, and this increased amount is quantitized and, if it is above a certain limit, is presumptive of the existence of the tumor.

Hormonally responsive cells release substances when receptors for the hormone bind the hormone. Likewise, certain analogs of such hormones, i.e., chemical variants of the hormone, are known to bind to the same receptor as the hormone itself, although the effects (agonize, antagonize, or other) may be unknown.

It is known in the art that GnRH agonist compounds, when chronically administered to patients having ovarian cancer, may over the long term result in a suppression of the disease and of tumor specific markers such as CA 125. Savino et al, "GnRH Analogs in Gynecological Oncology: A Review", *J. Chemotherapy*, 4(5):312–320 (1992). Thus, the art teaches that the administration of GnRH decreases the levels of tumor markers, even though it is known that GnRH analogs may stimulate the ovaries. Parinaud et al., "Paradoxical Ovarian Stimulations in the use of LHRH Analogs", *Eur. J. Obstet. Gynecol. Repro. Biol.*, 47:129–133 (1992). The art suggests that, with respect to human endometrial cell lines, GnRH analogs exert an antiproliferative effect measurable within the first 24 hours. Emons et al., "High Affinity Binding and Direct Antiproliferative Effects of Luteinizing Hormone-Releasing Hormone Analogs in Human Endometrial Cancer Cell Lines", *J. Clin. Endo. Metab.*, 77(6):1458–1464 (1993).

Serum ovarian cancer markers have not been as valuable as originally hoped for by the medical community. In standard tests, false positives occur with some frequency, especially in menstruating women with endometriosis or pelvic inflammatory disease. Since these conditions are relatively common and do not, by themselves, exclude a diagnosis of ovarian cancer, the usefulness of this test as a screen for the general population is limited. Moreover, positive results in a CA 125 test may also occur in other gynecologic malignancies and nongynecologic malignancies. Therefore, a positive result does not tell a treating physician if there is a tumor, or if present where it is or what type it is.

Standard tests are also limited in their usefulness by the occurrence of false negatives. Employing the standard testing method, up to 50% of early ovarian cancer may be unassociated with a rise in serum CA 125. This result is particularly unacceptable because a local stage I ovarian cancer has a 90% cure rate while an advanced ovarian cancer is associated with only a 35% five year survival rate.

It is known in the art to administer a compound to stimulate certain endocrine-tissue derived tumors, wherein response to the stimulation is measured by increased serum quantities of endocrine products of the tumor, which serve as specific markers, during a short period of time after administration of the compound. For example, it is known to administer calcium or pentagastrin to determine the presence of a possible thyroid medullary carcinoma, measuring serum calcitonin before and after administration, the resulting calcitonin level after stimulation being markedly increased. Barbot et al., "Pentagastrin Stimulation Test and Early Diagnosis of medullary Thyroid Carcinoma Using an Immunoradiometric Assay of Calcitonin: Comparison with Genetic Screening in Hereditary Medullary Thyroid Carcinoma ", *J, Clin. Endocrinology and Metabolism* (1994). Likewise, catecholamine release can be stimulated from pheochromocytoma (tumor of the adrenal medulla) by the administration of glucagon. Both of these tumors are believed to be primary endocrine neoplasms and may be related to each other and to parathyroid adenomas, in a familial (autosomal dominant) or a sporadic pattern. These tumors may also be related to neuroectodermal syndromes. Williams, *Textbook of Endocrinology*, W. B. Saunders, Philadelphia (1974) 306–316, 764–67, 1022–23.

The art does not teach stimulatory tests in general to screen for neoplasms. See, Deligdisch, Altchek & Cohen, *Atlas of Ovarian Tumors*, Igaku-Shoin, New York (1994)(Prepublication, a copy being provided as an appendix), incorporated herein in its entirety by reference. Accordingly there are no teachings of a screen for neoplasms using stimulatory tests in general, and especially with respect to ovarian, breast, prostatic, or pancreatic cancers.

With respect to ovarian cells, it is heretofore unknown that release of serum tumor marker can be differentially stimulated by administering hormone analogs, thus increasing the utility of such analogs in screening for tumors by distinguishing over non-ovarian sources of such markers. In particular, GnRH receptors are present on ovarian epithelial neoplasms as well as on normal ovarian tissue. Emons et al., "Gonadotrophin Releasing Hormone Binding Sites in Human Epithelial Ovarian Carcinomata", pp. 215–21; Ohno et al., "Presence of Gonadotrophin-Releasing Hormone and its Messenger Ribonucleic Acid in Human Ovarian Epithelial Carcinoma", *Am J. Obstet. Gynecol.*, 169:605–10 (1993); Adelson et al., "Effects of Gonadotropin-Releasing Hormone Analogs on Ovarian Epithelial Tumors", *Clin. Obstet. Gynecol.*, 36(3):690–700 (1993); Leung et al., "Intracellular Signalling in the Gonads", *Endocrine Reviews*, 13(3):476–498 (1992)(incorporated in its entirety by reference). Long term treatment of patients harboring these neoplasms with GnRH analogs has been associated over time with a decline in the tumor marker CA 125 thus suggesting a possible desensitization effect.

CA 125 is a high molecular weight, non-mucin cell surface glycoprotein complex of molecules that is present in forms varying from 220 to over 1000 kD. CA 125 is identified by a murine monoclonal antibody called OC 125. CA 125 has a serum half life of 4.5 days, and has an upper normal range of 35 U/ml.

The CA 125 antigen complex is normally found in cells from the coelomic epithelium, and may also be found in the epithelia of the pancreas, colon, gallbladder, stomach, lung and kidney. Various benign conditions may cause elevated CA 125 levels, including endometriosis, adenomyosis, leiomyoma, acute pelvic inflammatory disease, early pregnancy, menstruation and benign ovarian cysts.

The selectivity of CA 125 as a screen for cancer is limited, being 97% for a single serum assay, and the art has sought to improve screens employing serial testing, combinations of serum markers, and by adding pelvic examination and ultrasound. The sensitivity of CA 125 as a screen is only about 53%, which, of course suggests a large number of false negative results, which occur especially in stage I tumors. It is these early, stage I tumors which are desired to be detected because of their far improved prognosis. Therefore, CA 125 serum testing, as presently performed, is an inherently unreliable screen, with a low selectivity and a low sensitivity, and therefore is insufficient as presently devised.

The effects of the selectivity of a screen are apparent from the following analysis. Ovarian cancer has an incidence of 40 per 100,000 women over age 45 per year. Therefore, in order to achieve a 100% sensitivity, e.g. detection of all diseased patients, with at least 10% positive predictive value, e.g. no more than 9 false positives for each detected tumor, a 99.6% specificity value would be required. This is in contrast to the actual about 97% selectivity and about 50% sensitivity. Therefore, CA 125 remains experimental as a screen for ovarian cancer, missing many early tumors and requiring a follow-up of a large number of false positive results. However, CA 125 may have significant value in following post-treatment ovarian cancer, where a serum measurement is compared to a baseline measurement, thereby facilitating monitoring CA 125 levels as an indication of tumor mass, providing evidence of the efficacy of chemotherapy and providing an early indication of relapse. See Berkowitz, "CA125 Measurement in the Epithelial Ovarian Cancer: a 10-Year Anniversary of Clinical Investigation", *Gynecol. Onc.*, 49:1–2 (1993).

Other proposed serum indicators of ovarian tumors include inhibin activin, follistatin, Lipid-Associated Sialic Acid (LASA-P), CA 19-9, CEA, MB-70K, DM/70K (Dianon Systems, Inc. Stratford, Conn.), M-CSF, Urinary Gonadotrophin Factor, Ca 130 and PRL. See Bernstein et al., "Comparison of CA 125, Lipid Associated Sialic Acid (LASA-P), CA 19-9, and CEA in Monitoring Patients with Ovarian Cancer", *J. Tumor Marker Oncology*, 6(3):183–187 (1991); Miyanaga et al, "Differential Control of Activin, Inhibin and Follistatin Proteins in Cultured Rat Granulosa Cells", *Biochem. Biophys. Res. Comm.* 194(1): 253–258 (1993); Schwartz et al, "Circulating Tumor Markers in the Monitoring of Gynecologic Malignancies", *Cancer*, 60(3):353–361 (1987); Cole et al., "Urinary Gonadotropin Fragment, a New Tumor Marker", *Gynecol. Onc.* 36:391–94 (1990); Suzuki et al., "Macrophage Colony-Stimulating Factor as a Tumor Marker for Epithelial Ovarian Cancer", *Obstet. Gynecol.*, 82(6):946–950 (1993)(incorporated herein in its entirety by reference); Hosono et al., "Different Antigenic Nature in Apparently Healthy Women with High Serum CA 125 Levels Compared with Typical Patients with Ovarian Cancer", *Cancer*, 70(12):2851–2856 (1992). Other known markers include CA 15-3, CA 72-4, CA 54/61 and OVX-1. Negishi et al, "Serum and Tissue Measurements of CA72-4 in Ovarian Cancer Patients", *Gynecol. Onc.*, 48:148–54 (1993); Kobayashi et al, "Monoclonal Antibodies MA54 and MA61 as Potential Reagents in the Prognosis of Patients with Ovarian Cancer", *Gynecol. Onc.*, 49:80–85 (1993); Woolas et al, "Combinations of Multiple Serum Markers are Superior to Individual Assays for Discriminating Malignant from Benign Pelvic Masses", Preprint (incorporated herein in its entirety).

Inhibin, a naturally occurring peptide hormone is known to increase in quantities which, according to one study peak at 772±38 U per liter in the follicular phase of the menstrual cycle in pre-menopausal women, and is undetectable in most post-menopausal women. Lappöhn et al, "Inhibin as a Marker for Granulosa-Cell Tumors," *New England Journal of Medicine*, Vol. 312, No. 12, Sept. 21, 1989, pp. 790–793. See also Kauppila et al., "GnRH Agonist Analog Therapy in Advanced/Recurrent Granulosa Cell Tumors: Further Evidence of a Role of Inhibin in Monitoring Response to Treatment", *Gynecological Endocrinology*, pp. 271–274. Likewise, inhibin is believed to increase in serum level concentrations for patients with granulosa-cell tumors. Healy, et al., "Elevated Serum Inhibin Concentrations in Postmenopausal Women with Ovarian Tumors," *New England Journal of Medicine*, 329(21): 1539–42 (Nov. 18, 1993); Witt et al, "Endocrine Function of Granulosa Cell Tumors In Vivo", *Gynecol. Obstet. Invest.*, 33:59–64 (1992). Serum inhibin levels may be quantified according to the method of Medgenix Diagnostics, Fleurus, Belgium, described in Blaakaer et al., "Immunoreactive Inhibin-Production in Post-Menopausal Women With Malignant Epithelial Ovarian Tumors", *Eur. J. Ob. Gyn. and Reproductive Biol.*, 52 (1993) 105–110, incorporated herein by reference.

Hormones are generally considered to be circulating compounds which produce a specific biological effect on responsive cells. Hormones are detected by these responsive cells by means of receptors, which are generally on the cell surface or in the cytoplasm. Peptide hormones generally are bound to cell surface receptors, producing a secondary messenger signal, such as c-AMP, in the cell. Often, circulating hormones have a short half-life, since they are degraded, inactivated or removed from the circulation. In order to provide improved pharmacological properties of a drug which acts similarly to a natural hormone, modifications may be made to increase its binding to the receptor or increase its half-life. Compounds which closely resemble natural hormones with modifications and/or substitutions and having biological activity as receptor agonists or antagonists are known as hormone analogs. These analogs may be modified by replacing certain 1-amino acids with d-amino acid isomers or by derivatization. Hormone analogs also include amino acid substitutions and peptides having shorter or longer chain lengths.

While the endocrine system generally requires the transmission of a chemical message through the blood stream to a distant target organ, a paracrine signaling system also exists which allows chemical signaling between proximate cells, without requiring transmission through the blood stream. In many cases, endocrine hormones may also serve as paracrine hormones having a different function. Thus, the same or similar endocrine hormones having a defined effect on an endocrine target organ may also have unexpected paracrine or autocrine effects on various organs, if the hormone is functionally present in the intercellular space in sufficient quantities.

Large numbers of peptide hormone analogs are known, and the selection of a particular analog for biological or medicinal use is within the ordinary skill in the art once the receptor organ and the desired effect are identified. For example, in order to maximally stimulate tissues which are known to be responsive to GnRH (gonadotrophin releasing hormone), one skilled in the art would select a protease resistant GnRH receptor agonist. In particular, such hormone analogs are FDA approved, e.,g., Synarel and Nafarelin, and can be administered to patients. There are other examples of FDA approved peptide hormones, and a host of experimental and non-U.S. drugs available.

It is therefore an object of the present invention to provide a dosage form, method of administration, assay, screen, and kit for the general detection of neoplasms.

It is another object of the present invention to provide a dosage form, method of administration, assay, screen and kit for the detection of specific neoplasms, namely ovarian cancer, breast cancer, prostatic cancer, and pancreatic cancer.

Other and further objects of the invention will become apparent through a reading of the Summary, Detailed Embodiments and Claims, below.

SUMMARY OF THE INVENTION

The foregoing and other objects are achieved by the present invention, which involves the enhancement of tumor detection tests by the administration of a tumor specific stimulant to the patient prior to drawing a blood sample, thereby causing a measurable increase in the serum level of a tumor marker or tumor associated substance, a response not commonly seen in normal patients. The present invention also includes the packaging and formulation of dosage forms of tumor stimulating compounds in a manner particularly suited for use in a screening program. The present invention further includes the implementation of a screening program using the inventive enhanced-tumor detection tests by analyzing the results of a particular patient in view of the results obtained with the population-at-large.

The present screen allows increased sensitivity by stimulating the release of tumor markers, measured in the serum, by selectively stimulating the ovarian tissue. In addition, increased selectivity may be obtained because other non-ovarian tumor sources of CA 125 or other tumors and/or tumor markers, e.g. endometriosis, may have a lesser or opposite response to stimulation.

The inventive method is also useful for monitoring the treatment of post-treatment patients having tumors which can be differentially stimulated to release tumor markers in contrast to other interfering sources of the marker. The present invention also encompasses a method of stimulating a response from a known or suspected tumor in a patient by the administration of a tumor-stimulating agent, including a hormonal or paracrine stimulant in order to evaluate the prognosis and help devise a treatment for the patient.

In practice, the person tested may fall into one of three general categories: first, a member of the general population or a member of a selected subset of the population having a different, increased risk for a tumor; second, a person who has been possibly diagnosed with a cancer, but has not been definitively diagnosed; and third, a status post-cancer therapy individual.

In general, the stimulant compounds are safe and rarely have side effects; the side effects seen generally being non-fatal and non-permanent. Further, since the stimulant compound is administered only shortly before the test is conducted, the cumulative dose will be small, even if the immediate dose is high, in order to provoke a maximal response from the tumor. Thus, a dose of the stimulant should be given which is expected to significantly excite a responsive tumor and overcome any masking effect of interfering sources of the marker. In general, for stimulant drugs approved for other purposes, the dose will be between 10–400% of the recommended dose for other FDA approved indications, and will be administered at a time prior to measurement such that a significant and measurable effect can be observed. The period of administration of the stimulant prior to measurement is preferably less than 24 hours, and the formulation preferably provides for a single administration, which may be in the form of single or multiple dosage forms administered simultaneously or close in time.

It may also be preferable to simultaneously measure a number of parameters in the patient, e.g. the serum levels of a number of markers or hormones. Simultaneous detection assays are known to increase the selectivity of an assay.

In a preferred embodiment according to the present invention, the tumor to be screened for is an epithelial ovarian tumor, wherein the production of CA 125 and/or inhibin is stimulated by the administration of a GnRH analog between 1–24 hours prior to drawing blood. Blood samples are taken during the course of the twenty-four period, and the results reviewed to determine a stimulatory rise in the CA 125 and/or inhibin levels indicative of GnRH analog binding to receptor sites on the tumor, which in turn are stimulated to produce greater quantifies of the marker over a maximum normal value within that period.

The GnRH analogs applicable to the present invention include, but are not limited to: leuprolide, leuprorelin (D-Leu$^6$, des-Gly$^{10}$), nafarelin, goserelin, [D-Ala$^6$, des-Gly$^{10}$]-GnRH-ethylamide, buserelin (D-Ser(Bu$^t$)$^6$, des-Gly$^{10}$), GnRH-acetate, triptorelin (D-Trp$^6$), and [D-p-Glu$^1$, D-Phe$^2$, D-Trp$^{3,6}$]-GnRH, H4055 (des-Gly$^{10}$), H4065(D-Trp$^6$, des-Gly$^{10}$), ovurelin (D-Phe$^6$), and decapeptyl (D-Trp$^6$).

Other embodiments include screens for breast, prostate and pancreatic cancer through the same methodology involving organ-specific stimulant administration and quantitized assay of appropriate tumor-specific marker within a short period of time post-administration to determine stimulatory response indicative of tumor. For example, GnRH receptors may be found in breast cancer, see Emons, et al., "LH-RH Agonists in the Treatment of Ovarian Cancer", Recent Results in Cancer Res., 124:55–68 (1992), thus indicating the potential for GnRH stimulation of certain breast tumors.

Thus, the present invention includes an understanding that any improvement in the sensitivity and/or selectivity of the use of a tumor marker is of significant value, and that the hormone and paracrine response differences between normal and malignant tissues to a stimulant may be utilized in order to diagnose the condition through a stimulatory test. Further, the improvement in the selectivity and sensitivity allows the use of previously known or proposed tumor markers for the screening of the general population.

DETAILED DESCRIPTION OF THE PREFERRED EMBODIMENTS

While the dosage form, method of administration, assay, screen and kit are generally viable for the detection of various neoplasms, a preferred embodiment of the invention involves the detection of ovarian cancer through stimulatory tests utilizing GnRH analogs wherein assays are employed to test for increased production of various markers, preferably CA 125 or inhibin, in quantizable amounts, which are then determined to be indicative of tumor.

Accordingly, the screening test for inhibin production in accordance with a preferred embodiment of the invention, involves the administration to a target population of a stimulating agent and the test for greater production of CA 125 or inhibin (compared to a normal control group) indicating the existence of ovarian cancer cells.

The target population to be assayed includes generally any female, pre- or post-menopausal and pre- or post-symptomatic of ovarian cancer. Thus the population can range from normal, healthy young adults through geriatric women, and those who have already been diagnosed as having ovarian cancers and are post-operative.

The stimulating agent employed herein is generally any agent that will produce a significantly greater quantitative increase in inhibin or CA 125 production over a baseline that is either specific to the patient or general based upon a statistical normal created through population data base information. Care is obviously taken to compensate for, or eliminate the effects of physiological menstrual cycle variation in inhibin release.

To summarize the preferred embodiment, a dosage form, method of administration, assay, screen and kit for detection of ovarian cancer in accordance with the invention possesses the following steps: (1) selection of a GnRH analog (preferably leuprolide or nafarelin; (2) administration of the GnRH analog in sufficient quantities to cause an expected stimulatory response of a known tumor marker (selected from the group consisting of CA 125, inibin, LASA-P, CA 19-9, CEA, M-CSF, and preferably inibin or CA 125) either subcutaneously (leuprolide) or intranasally; and (3) assaying serum within the twenty-four hours of administration to determine significant increases in serum levels of the marker over a base line, thereby indicating tumor. In particular, leuprolide is administered subcutaneously in a quantity of between 0.05 mg and 500 mg., preferably 0.1 mg and 20 mg, and more preferably 1 mg. Nafarelin is administered intranasally in an amount of between 20 μg and 200 mg, and preferably 50 μg and 800 μg, and more preferably 400 μg. For an assay involving inhibin, a three fold rise (to about 300 units/1 from a baseline of about 122 units/1 in a post-menopausal women) would be suggestive of tumor. For an assay involving CA 125, a rise from about 35 units/ml to 100 units/ml would be suggestive of tumor.

The presently preferred procedure for proving efficacy of the procedure for assaying for ovarian cancer, utilizing inhibin or CA 125 is as follows. Three populations of women are selected. The first group consists of a control group of women without known ovarian tumors. The second group consists of women who have been possibly diagnosed as having ovarian cancer and who are scheduled to undergo laparotomy. The third group of women includes individuals who have previously been diagnosed and treated for ovarian cancer, who have a residual tumor mass.

Baseline serum markers are obtained. The sample is measured for CA 125, inhibin and other markers. After the sample is drawn, the women are administered a stimulatory dose of a long-acting GnRH analog. This analogs is either leuprolide, (Lupron) TAP pharmaceutical, subcutaneously 0.2 ml (1 mg dose) or a single spray in each nostril of nafarelin nasal solution, (Synarel) Syntex (200 μg per spray, total dose 400 μg).

Three repeat blood samples are drawn from each patient, one at each of 1, 2–4 and 12–24 hours after administration of the GnRH analog. The blood samples are then analyzed to determine the levels of ovarian tumor markers, especially CA 125 and inhibin. Known assays for CA 125 include those available from Abbott Laboratories, Chicago, Ill. and Centocor Inc., Malvern, Pa. The serum marker levels are then correlated with the presence and type of ovarian neoplasm present as well as the stage and grade of such tumors.

It is expected that both CA 125 and inhibin will correlate with disease. Further, the diseased patients will have a significantly higher level of circulating tumor markers, especially between 4 and 24 hours post stimulation, as compared to normal controls. As stated above, the levels of CA 125 will rise to approximately three times the upper limit of normal value as known in the art from a normal upper limit level of 35 U/ml to approximately 100 U/ml in responsive diseased patients. In postmenopausal diseased subjects, inhibin levels are also expected to rise about 300% above the upper limit of normal. The upper limit of normal baseline serum inhibin level is about 122 U/l. Pre-stimulation, diseased patients will show an approximately 10% increased level of inhibin. Post-stimulation, the undiseased patients will show an approximately 50% rise in inhibin, while diseased responsive patients will show an approximately 300% rise, at sample points between 2–4 and 16 hours after stimulation. In premenopausal women, the study is conducted at a portion of the menstrual cycle in which the inhibin levels are naturally lower, and a three-fold increase in serum inhibin above the upper limit of normal is then expected in women with responsive ovarian cancers. The normal menstrual cycle is preferably compensated in this manner, as inhibin may rise to an average of approximately 770 U/1 at its peak, and therefore could possibly mask the stimulatory effects of the GnRH analog stimulation or reduce the quality of the screen. Lappöhn, et al, "Inhibin as a Marker for Granulosa-Cell Tumors," *New England Journal of Medicine*, Vol. 312, No. 12, Sep. 21, 1989, pp. 790–793. See Fraser et al., "Does Inhibin Have an Endocrine Function During the Menstrual Cycle", *TEM* 4(6):187–194 (1993). It is noted that ovarian granulosa cell tumors are derived from endocrine tissue and are relatively uncommon and the production of inhibin by granulosa cell tumors in response to stimulation is not particularly the subject of the present invention, although various aspects of the invention my relate to these tumors in a novel manner. Rather, the present invention is related to the detection of ovarian epithelial cell carcinomas, which are not derived from endocrine tissue.

It should also be noted that the marker release may also be stimulated in a number of ways: first, hormonally active compounds may be used to stimulate tumors which are hormonally responsive. Second, another drug which targets tumor receptors may be administered. Third, drugs which target the tumor cell in another manner may be administered. Fourth, stimulation of the tumor may be mechanical, by way of palpation, acoustic shock wave, vibration or percussion. Fifth, the tumor may be stimulated by a change in temperature, e.g. hyperthermia, which may be induced by ultrasound, microwaves, electrotherapy or other methods. Sixth, an electrical or electromagnetic field may stimulate the tumor tissue. It should also be noted that cytokines may be administered to stimulate the tumor, and related molecules may serve as tumor markers as well. Grosen et al., "Measurement of the Soluble Membrane Receptors for Tumor Necrosis Factor and Lymphotoxin in the Sera of Patients with Gynecological Malignancy", *Gynecol. Oncol.*, 50:68–77 (1993). While cytokine stimulation may be less specific for tumor cells than other regimens, it is possible that a tumor of unknown type will respond to a cytokine even if a specific cellular receptor cannot be identified. In such a case, specificity must be obtained by careful selection and analysis of the serum marker levels.

The present invention also includes various therapeutic modalities which are derived from the knowledge that a tumor possess certain receptors on its cell surface which are not widespread. In this instance, such as the GnRH receptors found in ovarian cancers, a cytotoxic therapy regimen could be directed to the malignancy based on a chemotherapeutic receptor binding compound. Care should be taken, however, to avoid destroying vital nontumor tissue which possesses the same receptors. This may be accomplished by local infusion therapy, masking of non-tumor receptors, or a secondarily activated agent which becomes toxic only after excitation, the excitation being limited to the body region where the tumor is present. Of course, other treatments which are selective for the tumor and which employ receptor-specific binding to target the tumor are within the scope of this invention.

The present invention also includes the diagnosis of tumors, especially ovarian tumors, by the administration of a tagged receptor binding compound. The compound may be a hormone, hormone analog, hormone antagonist or other moiety which specifically binds to receptors selectively expressed in quantity on the surface of particular tumor cells. The tag may be a radio-isotope, such as indium-111, technetium-99, iodine-123, iodine-131, gallium-72, or other isotope with a short half-life which is linked to the receptor binding moiety. Indium-111 is a preferred isotope, and iodine-123 is preferred to iodine-131, due to its shorter half-life. In addition, it is also possible to detect other radioactive compounds. In practice, the radio-labelled receptor-binding moiety (tracer) is administered to the patient, and will be distributed in the tissues according to receptor density and normal catabolic activities. A scintillation or other type of scan is performed a short time after administration of the tracer. Since the tracer is generally a derivatized known hormonally active compound, the normal locations of high density receptors must be compensated for. Any abnormal localization of radio-isotope or an abnormal distribution thereof may be detected and the patient subjected to further diagnostic workup. This radio-isotope scanning method is generally limited to patients with known tumors or with a suspected or high probability of tumor, due to the costs, inherent hazards and inconvenience of this procedure.

According to the present invention, a paramagnetic atom of a receptor binding composition (tracer) may be detected by means of an MRI scan. In principle, the tracer includes, either inherently or as a derivative, substitution or isotope a paramagnetic atom which is relatively unique or easily distinguishable from the background. In this case, for instance, hydrogen would not be preferred because it is ubiquitous in biological tissues. The tracer is administered to the patient, and after allowing sufficient time for binding to any receptors, the patient is subjected to an MRI scan in an apparatus tuned to detect the tracer. Any abnormal localization or distribution of the tracer may thereby be detected and the patient subjected to further diagnostic workup.

Other imaging techniques may also be employed to detect occult tumors, as known in the art, such as PET scanning and the like, using the methods according to the present invention. The preferred positron-emitting isotope is fluorine, which has a half-life of about 20 minutes. Helium-3 or other known suitable isotopes may also be used.

Various hormones may be used to stimulate marker release from tumors. Various neoplasms have receptors for EGF, cytokines, TNF, M-CSF, G-CSF, CCK, secretin, oxytocin, FSH, TRH, insulin-like growth factor (IGF-I), HCG, PTH, bFGF, NPY, CRF or somatostatin. In addition, tumors may be responsive to either corticosteroids or gonadal steroids, including estrogen, testosterone and dihydrotestosterone. Thus, for example, an occult pancreatic tumor might be stimulated and therefore be detectable after administration of CCK or secretin. Likewise, other tumors may be responsive to various hormones.

While the prior art has established that tumors arising from endocrine glands may aberrantly produce hormones, and may be stimulated to release these hormones, such as multiple endocrine neoplasia type II (MEN-II), discussed above with respect to thyroid medullary carcinoma and pheochromocytoma, the present invention is directed to two aspects of tumors. First, tumors are stimulated to produce cancer markers, such as CA 125, which are not necessarily active as hormones, and are generally not detected on the basis of any measured hormonal activity. Second, neoplasms without a known relationship to any parent cell having endocrine differentiation features are stimulated to produce markers which may be hormonally active, such as inhibin production by ovarian epithelial carcinomas. Thus, the present invention is distinguished from these known stimulation tests. Further, the present invention additionally relates to a screen for tumors, while the prior art does not teach or suggest that a stimulation test may be employed as a cancer screen in the general population. See Becker, Ed., *Principles and Practice of Endocrinology and Metabolism*, J. B. Lippincott Co. (1990), Ch. 221:1626.

Various tumors arise from non-endocrine cell lines which may produce hormones, including various lung cancers, especially small cell carcinoma, prostatic cancer, neural tumors, thymomas and melanomas. This production has been termed "ectopic", however studies have revealed that peptide hormones may be present as paracrine hormones in many tissues. Thus, based on past experience (many tissues are associated with identified paracrine hormone substance production), and that in tissues in which a paracrine hormone has been identified, these same tissues may also be associated with receptors for the hormone (or a biologically related hormone). Therefore, in certain types of tumor tissues, there are receptors that can be stimulated by application of hormones or analogs thereof. According to the present invention, tumor tissues which are responsive to hormones and capable of producing certain circulating tumor markers will release increased levels of circulating markers after stimulation. Accordingly, tumor tissues may be responsive to hormones and produce detectable substances, including peptides as markers, in response to these hormones. According to the present invention, the stimulation of the tumor tissue prior to serum tumor marker measurement will lead to increased levels of markers, which will possibly allow for a greater sensitivity for detection of tumors, and greater selectivity due to a differential level of response from tumor and non-tumor tissue.

A distinguishing factor between endocrine and paracrine hormones is that endocrine hormones employ the blood stream to distribute the hormone to other tissues, while paracrine hormones are released into the intercellular space for a local effect and only incidentally reach the blood stream, and then usually at low levels. Thus, the present invention includes the stimulation of the paracrine system which may be present in tumors to induce a differentially detectable effect.

In likewise manner, a screen or test may be conducted to determine the effect of a stimulation of an epithelial ovarian tumor to increase circulating levels of other tumor markers, using known methods of measurement to determine blood levels.

Further, tumors of breast, prostam and pancreas may also be detected by administering a tumor stimulant, which is selected by determining a receptor found on a significant proportion of tumors in the population, selecting a drug or agent which will cause a stimulation of the cell as a direct or indirect result of interaction with the tissues, and thereafter waiting for a significant response and measuring the response.

The present invention also includes a screening kit which allows a physician to screen a single patient for a disease, the kit including a quantity of the stimulant sufficient for the patient, to be administered prior to drawing a blood sample. The kit optionally includes paraphernalia for drawing a blood sample, and/or a shipping container for forwarding the sample to a laboratory.

According to the present invention, a testing laboratory defines a population norm based on the history of use of the assay in a normal population in order to assist a physician in interpreting the result. A database of information must be analyzed in distinguish normal from abnormal, although a physician may be presented with only a single datum.

The above description and preferred embodiments are provided not to limit the invention but to assist one skilled in the art in better understanding the invention contained herein. The inventor is not thereby limited to the preferred embodiments, but is only limited by the scope of the claims below. One of reasonable skill in the art can also practice the invention through other and equivalent methods, compositions and techniques which are, as well, included within the scope of the invention, to the extent set forth in the appended claims.

We claim:

1. A method for screening for presence of tumor cells in a subject, wherein said tumor cells are derived from cells which do not have endocrine differentiation features, comprising:
   (a) administering an amount of a tumor stimulating hormone to said subject in an amount sufficient to provoke production of a tumor marker by said tumor cells, and
   (b) determining said tumor marker in a sample taken from said subject, wherein an increase in amount of said tumor marker relative to normal levels thereof is indicative of possible presence of tumor cells in said subject.

2. The method of claim 1, wherein said tumor cells are ovarian cancer cells.

3. The method of claim 1, wherein said tumor marker is selected from the group consisting of CA125, inhibin, LASA-P, CA19-9, CEA, MB-70K, DM/70K, urinary gonadotropin factor, Ca130, PRL and M-CSF.

4. The method of claim 1, wherein said sample is a serum sample.

5. The method of claim 1, wherein said sample is a blood sample.

6. The method of claim 1, wherein said tumor stimulating hormone is selected from the group consisting of leuprolide, leuprorelin, nafarelin, goserelin, [D-Ala$^6$, des Gly$^{10}$]-GnRH-ethylamide, buserelin, GnRH-acetate, triptorelin, [D-p-Glu$^1$, D-Phe$^2$, D-Trp$^{3,6}$]-GnRH, H4055, H4065, ovurelin, and decapeptyl.

7. The method of claim 1, wherein said tumor stimulating hormone is administered subcutaneously or intranasally.

8. The method of claim 2, wherein said tumor cells are cells of an occult tumor.

9. The method of claim 6, wherein said tumor stimulating hormone is leuprolide.

10. The method of claim 9, comprising administering leuprolide subcutaneously.

11. The method of claim 9, comprising administering said leuprolide in an amount ranging from 0.05 mg to 500 mg.

12. The method of claim 11, comprising administering from 0.1 mg to 20 mg of leuprolide.

13. The method of claim 6, wherein said tumor stimulating hormone is nafarelin.

14. The method of claim 13, comprising administering nafarelin nasally.

15. The method of claim 12, comprising administering from 20 ug to 200 mg of nafarelin.

16. The method of claim 15, comprising administering from 50 ug to 800 ug of nafarelin.

* * * * *